United States Patent [19]

Broer et al.

[11] Patent Number: 5,767,370

[45] Date of Patent: *Jun. 16, 1998

[54] DEACETYLASE GENES FOR THE PRODUCTION OF PHOSPHINOTHRICIN OR PHOSPHINOTHRICYL-ALANYL-ALANINE, PROCESSES FOR THEIR ISOLATION, AND THEIR USE

[75] Inventors: Inge Broer; Doris Hillemann; Alfred Pühler; Wolfgang Wohlleben, all of Bielefeld; Günter Donn, Hofheim am Taunus; Hubert Müllner, Kelkheim; Klaus Bartsch, Steinbach, all of Germany

[73] Assignee: Hoechst Aktiengesellschaft, Frankfurt, Germany

[ * ] Notice: The term of this patent shall not extend beyond the expiration date of Pat. No. 5,668,297.

[21] Appl. No.: 459,254

[22] Filed: Jun. 2, 1995

Related U.S. Application Data

[62] Division of Ser. No. 279,705, Jul. 25, 1994, abandoned, which is a continuation of Ser. No. 146,803, Nov. 1, 1993, abandoned, which is a continuation of Ser. No. 926,498, Aug. 7, 1992, abandoned.

[30] Foreign Application Priority Data

Aug. 9, 1991 [DE] Germany .................. 41 26 414.2

[51] Int. Cl.[6] .................. A01H 5/00; C12N 5/14; C12N 15/31; C12N 15/52; C12N 15/82
[52] U.S. Cl. .................. 800/205; 47/58; 435/172.3; 435/320.1; 435/419; 536/23.2; 536/23.7
[58] Field of Search ................ 435/6, 30, 32, 435/36, 172.3, 320.1, 419; 536/23.2, 23.7; 800/205; 47/58

[56] References Cited

FOREIGN PATENT DOCUMENTS 0-257 542 B1   3/1988   European Pat. Off. .

WO-A-90 08828   8/1990   WIPO .
WO-A-91 03561   3/1991   WIPO .

OTHER PUBLICATIONS

Strauch et al., Gene 63, pp. 65–74 (1988).
Hara et al., Journal of General Microbiology 137(2), pp. 351–359 (1991).
Wohlleben et al., Gene 70, pp.25–37 (1988).
Bender et al., J. of Bacteriology, vol. 129, No. 2, pp. 1001–1009 (1977).
Baumberg, S., Molec. Gen. Genetics 106, pp. 162–173 (1970).
Delic et al., Mutation Research 9, pp. 167–182 (1970).
Drake and Baltz, Ann. Rev. Biochem. 45, pp. 11–38 (1976).
Kleckner, N., Ann. Rev. Genet. 15, pp. 341–404 (1981).
Mariani et al., Nature 347, pp. 737–741 (1990).
Koltunow et al., The Plant Cell 2, pp. 1201–1224 (1990).
Murakami et al., Molec. Gen. Genetics 205, pp. 42–50 (1986).
Potrykus, Bio/Technology 8, pp. 535–542 (1990).
Embel Sequence Database Acc. No. X65195 (Apr. 10, 1993).
Raibaud et al., Journal of Bacteriology 173(14), pp. 4454–4463 (1991).

*Primary Examiner*—Douglas W. Robinson
*Assistant Examiner*—Amy J. Nelson
*Attorney, Agent, or Firm*—Frommer Lawrence & Haug LLP

[57] ABSTRACT

Deacetylase genes for the production of phosphinothricin or phosphinothricyl-alanyl-alanine, processes for their isolation, and their use.

The invention relates to deacetylase genes, to processes for their isolation, and to their use, in particular for the production of transgenic plants using tissue-specific promoters. It is possible to prevent the development of certain parts in these plants in a targeted manner. With the aid of deacetylase genes, it is furthermore possible to identify and isolate tissue-specific promoters in transgenic plants.

25 Claims, 2 Drawing Sheets

DEACETYLASE GENES FOR THE PRODUCTION OF PHOSPHINOTHRICIN OR PHOSPHINOTHRICYL-ALANYL-ALANINE, PROCESSES FOR THEIR ISOLATION, AND THEIR USE

This application is a division of application Ser. No. 08/279,705, filed Jul. 25, 1994, now abandoned, is a continuation of application Ser. No. 08/146,803, filed Nov. 1, 1993, now abandoned, which is a continuation of application Ser. No. 07/926,498, filed Aug. 7, 1992, now abandoned.

Deacetylase genes for the production of phosphinothricin or phosphinothricyl-alanyl-alanine, processes for their isolation, and their use.

The invention relates to deacetylase genes, to processes for their isolation, and to their use, in particular for the production of transgenic plants using tissue-specific promoters. In these plants, the development of certain parts can be prevented in a targeted fashion. With the aid of deacetylase genes, it is also possible to identify and isolate tissue-specific promoters in transgenic plants.

BACKGROUND OF THE INVENTION

Phosphinothricin (PTC, 2-amino-4-methylphosphinobutyric acid) is a glutamine synthetase (GS) inhibitor. PTC is a "building block" of the antibiotic phosphinothricyl-alanyl-alanine. This tripeptide (PTT) is active against Gram-positive and Gram-negative bacteria and also against the fungus Botrytis cinerea. PTT is produced by the strain Streptomyces viridochromogenes Tü494 which has been deposited at the Deutsche Sammlung für Mikro-organismen [German Collection of Microorganisms], from where it can be obtained; Deposit Nos. DSM 40736 and DSM 4112.

German Patent 2,717,440 discloses that PTC acts as a total herbicide. The published application (EP-A-0,257,542) describes how herbicide-resistant plants are produced with the aid of a phosphinothricin-N-acetyl-transferase (pat) gene. The phosphinothricin-N-acetyl-transferase encoded by the pat gene modifies the intracellular PTC and detoxifies the herbicide.

SUMMARY OF THE INVENTION

The present invention describes deacetylase genes (dea), whose expression products are capable of deacetylating N-acetyl-phosphinothricin (N-Ac-PTC), or N-Ac-PTT, intracellularly, whereupon the antibiotic activity of these compounds is restored.

An N-acetyl-phosphinothricin tripeptide deacetylase gene according to the invention can be isolated from S. viridochromogenes Tü494. The dea gene is located downstream of the pat gene on the 4. 0 kb BamHI fragment, which has already been disclosed (EP-A-0,257,542). This gene is located on a BglII-BamHI fragment and is specified in detail by the sequence (FIG. 1 and Table 1). The protein sequence is defined by the DNA sequence. An ATG codon which is recognized in bacteria and in plants acts as the translation start codon; the Shine-Dalgarno sequence is emphasised by underlining. This gene codes for the last step in PTT biosynthesis, namely the deacetylation of inactive N-acetyl-phosphinothricin tripeptide to give the active PTT.

TABLE 1

| Bgl II | RBS | Met | | | |
|---|---|---|---|---|---|
| AGATCTGAGC | GGAGAGCGCA | TGGCATCGTC | GGAGTTGGAG | CTGGTGCGGG | AACTGATCGG |
| GCTCAACTGG | CACACCCGCA | ACGGCGATGT | GGAGCCACGC | CGGGTGGCCT | ACGACCGAGC |
| CCAGGAGGCC | TTCGGGCACC | TGGGCCTGCC | CCCCGGCGAG | ACCGTCGTGA | TCGGCGACTG |
| CTCGGCGGAG | TGGGTACGGC | CCGCCCAGGA | GGACGGCAGG | ACCCTGCTGT | ACCTGCACGG |
| CGGTTCGTAC | GCCCTCGGAT | CGCCGCAGTC | GCACCGCCAT | CTGTCCAGCG | CGCTGGGCGC |
| GGCGGCCGGG | GCGGCGGTGC | TCGCCCTGCA | CTACCGCAGG | CCGCCCGAGT | CTCCCTTCCC |
| GGCGGCGGTG | GAGGACGCCG | TGGCGGCCTA | CCGGATGCTG | CGGGAGCGGG | GCCTGCCGCC |
| GGGGCGGATC | ACCTTCGCCG | GTGACTCGGC | CGGCGCGGGC | CTCGCCGTCG | CCGCCCTCCA |
| GGTGCTGCGC | GACGCCGGGG | ACCCGCTGCC | GGCCGCCGCG | GTGTGCATCT | CGCCCTGGGC |
| CGACCTGGCC | TGCGAGGGCG | CCTCGCACGT | CACCCGCAAG | GAGCGCGAGA | TCCTCCTGGA |
| CACCGAGGAC | CTGCTCCGCA | TGGCGGGGCG | CTACCTGGCC | GGCACCGATC | CCAGGAACCC |
| CCTGGCCTCG | CCCGCCCACG | GCGATCTGAC | CGGTCTGCCG | CCGCTGCTCA | TCCAGGTCGG |
| TTCCGAGGAA | GTCCTGTACG | ACGACGCCCG | GGCGCTGGAA | CAGGCGGCGC | TCAAGGCGGG |
| CGTACGGGTC | ACCTTCGACG | AGTGGCCGGA | GATGTTCCAC | GTCTGGCACT | GGTACCACCC |
| GGTGCTCCCC | GAGGGGCGTGC | CGCCGTCGAG | ACGGCGGGCG | TGTTCCTGCG | CCGCGCCACC |
| GAGGAGGGCG | AGCGGTGACC | GACTGGATCC | T | | |
| | Stop | | BamHI | | |

It is known of many enzymes that their specificity is not limited to one substrate. For example, the phosphinothricin-N-acetyl transferase, which is encoded by the pat gene, is actually used in PTT biosynthesis for the acetylation of desmethyl-PTC and can be used for the detoxification of PTC due to its non-specificity. Super-expression of the dea gene (with the aid of suitable promoters or by cloning onto high-copy vectors) it is now possible to use an N-acetyl-PTT-deacetylase of insufficient specificity for activating N-acetyl-phosphinothricin.

Another dea gene can be obtained from E. coli. In fact, it has been found that, in contrast with other bacteria (for example rhizobia and streptomycetes), no activity can be detected in the so-called PAT assay (Ph.D. thesis Inge Broer. Faculty of Biology. University of Bielefeld. Expression des Phosphinthricin-N-Acetyltransferase-Gens aus Streptomyces viridochromogenes in Nicotiana tabacum [Expression of the phosphinothricin-N-acetyltransferase gene from Streptomyces viridochromogenes in Nicotiana tabacum], p. 42–43, 1989) after cloning the pat gene into suitable expression vectors (Strauch et al., Gene, 63, 65–74, 1988; Wohlleben et al., Gene, 70, 25–37, 1988). Moreover, a low number of copies of the pat gene in E. coli is incapable of imparting PTT resistance since the endogenic deacetylase compensates for the action of the phosphinothricin-N-acetyltransferase. Finally, this deacetylase activity can be detected directly by the effective inhibition of the GS activity after an addition of N-acetyl-phosphinothricin. N-Ac-PTC is reacted by the deacetylase to give PTC, which then inhibits the GS in the known manner, which can be measured in the γ-glutamyl transferase assay (Bender et al., J. Bacteriol. 129, 1001–1009, 1977). This is due to an endogenic deacetylase activity of E. coli.

It should be assumed that this activity cannot be found in the argE mutant, which is known from the literature (Baumberg, Molec. Gen. Genetics 106, 162–173, 1970). Other E. coli deacetylase mutants can be selected easily: following traditional (Delić et al., Mut. Res. 9, 167–182, 1970; Drake and Baltz, Ann. Rev. Biochem. 45, 11–38, 1976) or Tn5 mutagenesis (Kleckner, Ann. Rev. Genet. 15, 341–404, 1981), such mutants can be recognised on PTT-supplemented minimal medium by the fact that they can only grow after transformation with a pat gene cloned into a low-copy vector.

Accordingly, the deacetylase gene can be isolated from E. coli by producing a gene bank, for example in the argE mutant of E. coli, or in a recently isolated mutant, using conventional processes (Maniatis et al., Molecular Cloning: a Laboratory Manual, Cold Spring Harbor Laboratory, Cold Spring Harbor, N.Y., 1982).

Methods for isolating further deacetylase genes result from the above text: for example isolation of novel organisms which are PTT-sensitive despite the presence of a pat gene on a low-copy vector, followed by isolation of a deacetylase gene.

In a further aspect of the invention, pat genes and dea genes can be used together with tissue-specific promoters to prevent the development of certain plant tissues in a targeted fashion. A specific use is, for example, the production of male-sterile plants.

The production of hybrid seeds in plant breeding depends on the guaranteed avoidance of selfing of the mother plant. In many plant species, male-sterile mutants occur naturally, and these are used in breeding. The molecular mechanism of male sterility (ms) remains insufficiently explained as yet. Moreover, no ms variants exist in a large number of cultivated varieties such as, for example, Beta vulgaris. It is therefore of great interest for agriculture to produce defined ms (male sterility) mutants of all important cultured varieties by way of molecular genetics. The company PGS/Belgium has proposed such a method in Patent Application PCT/EP 89/00495. It is based on the destruction of the tissue surrounding the pollen mother cells (tapetum). To this end, an RNAase gene is fused with a tapetum-specific promoter (Mariani et al.; Nature 347, 737–741, 1990). The exclusive expression of the gene in tapetum cells provides the selective destruction of tissue and thus prevents the formation of mature pollen. A plant carrying this gene should only be able to produce seeds after cross-fertilization. An essential shortcoming of this system is the fact that progeny of this plant are also male-sterile and can therefore not form seeds in the field, where they depend on selfing. This is only successful when the male partner of the crops carries a gene which can compensate for the action of the RNAase in the progeny. According to the above-mentioned disclosed patent application, this is supposed to be effected by the barstar gene. The fact remains that only genetically modified, i.e. transgenic, partners can be used in the cross.

The text hereinafter proposes methods for the production of ms (male sterility) plants which allow transgenic mother plants to be crossed with any partners of the same species. This is achieved by combining a dea gene which is under the control of, for example, a tapetum promoter, in connection with a constitutively expressed pat gene. Application of PTC, or PTT, results in a targeted inhibition of the glutamine synthethase in the tapetum cells, causing their death. An even simpler system consists in the production of transgenic plants which contain only a single foreign gene, namely a dea gene under the control of a tissue-specific promoter, in this case a tapetum promoter, and application of N-Ac-PTC, or N-Ac-PTT, to the plant.

Generally speaking, the invention accordingly comprises the following methods for the tissue-specific inhibition with the aid of a deacetylase gene, preferably the above-mentioned dea gene from E. coli or S. viridochromogenes Tü494:

1) Plants which are resistant to PTT or PTC by pat activity (for example produced as described in EP 0,257,542) are transformed with the deacetylase gene from streptomycetes under the control of a plant-tissue specific promoter. Application of PTT or PTC leads to the expression of the deacetylase gene for compensating for the phosphinothricin-N-acetyltransferase activity in the respective tissues. These are then destroyed selectively, while the remaining plant is resistant.

2) PTT- or PTC-resistant plants are transformed with the E. coli deacetylase gene under the control of a tissue-specific promoter. Application of PTT or PTC leads to the expression of the deacetylase gene for compensating for the phosphinothricin-N-acetyltransferase activity in the respective tissues. These are then destroyed selectively, while the remaining plant is resistant.

The use of N-acetyl-phosphinothricin, or N-acetyl-phosphinothricin tripeptide, can simplify this system. Both substances are not active as herbicides, but are taken up by plants, translocated and not degraded immediately. Deacetylase activity for N-acetyl-phosphinothricin and N-acetyl-phosphinothricin tripeptide has not been detected in plants as yet. The above-described 2-gene system can therefore be reduced to a 1-gene system and thus greatly simplified as illustrated further below:

3) Any plants are transformed with a deacetylase gene from streptomycetes under the control of a tissue-specific promoter. After application of N-acetyl-phosphinothricin or N-acetyl-phosphinothricin tripeptide, the tissue-specific expression leads to the immediate death of the respective tissue.

4) Any plants are transformed with a deacetylase gene from E. coli under the control of a tissue-specific promoter. After application of N-acetyl-phosphinothricin or N-acetyl-phosphinothricin tripeptide, the tissue-specific expression leads to the immediate death of the respective tissue.

Since the specificity of the deacetylase from streptomycetes for N-acetyl-phosphinothricin tripeptide is higher, it will be preferred to use N-acetyl-phosphinothricin tripeptide in case 3) and N-acetyl-phosphinothricin in case 4) if high activities are required. Tissue-specific promoters which can be used are all described promoters where selective expression in certain tissues has been detected (for example Koltunow et al., The Plant Cell., Vol. 2, 1201–1224, 1990). All newly-isolated promoters with similar properties are of course, also suitable. Other promoters which are suitable in addition to tissue-specific promoters are those which are subject to a different type of regulation (for example time-dependent, stress-dependent, environment-dependent) and which is tissue-specific.

These methods furthermore allow analysis of the differentiation of cell regulation and the production of plants in which the development of certain parts was inhibited in a targeted fashion, preferably the production of male-sterile plants.

A further application is the use of a dea gene for the identification of selectively expressed promoters. If DNA fragments with promoter activity are cloned upstream of dea genes, then the selective disappearance of parts of tissue after application of N-acetyl-phosphinothricin or N-acetyl-phosphinothricin tripeptide indicates the specificity of the promoter.

Finally, the invention relates to positive selection systems. Those cells in which the dea gene has been inactivated can be selected either in combination with the pat gene and PTT (or PTC) together with a dea gene or with N-acetyl-phosphinothricin (or N-acetyl-phosphinothricin tripeptide) and a dea gene alone. This allows successful cloning (insertion inactivation), but also rare events (for example transposition), to be selected directly. Other aspects of the invention are mentioned in the examples.

EXAMPLES

Figure 1:
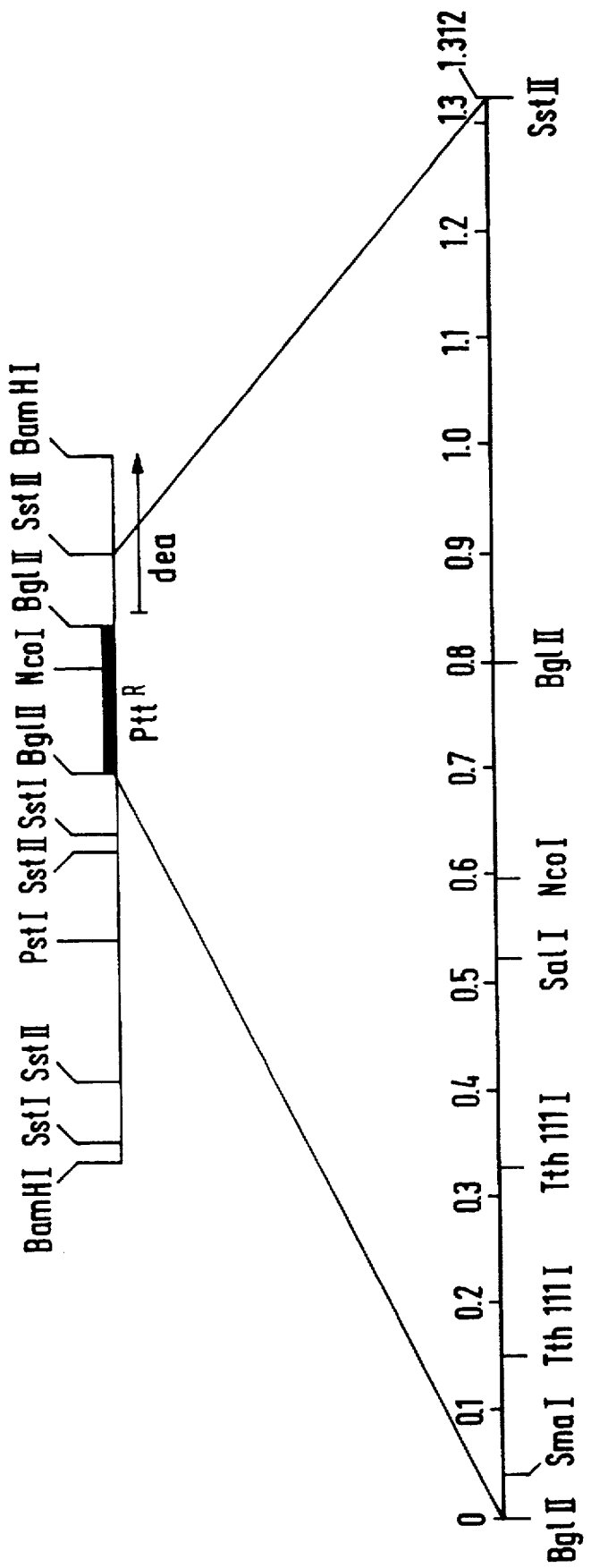
FIG. 1 shows a restriction map of DNA from cleaving pPRI with BamHI and BgIII.
Figure 2:
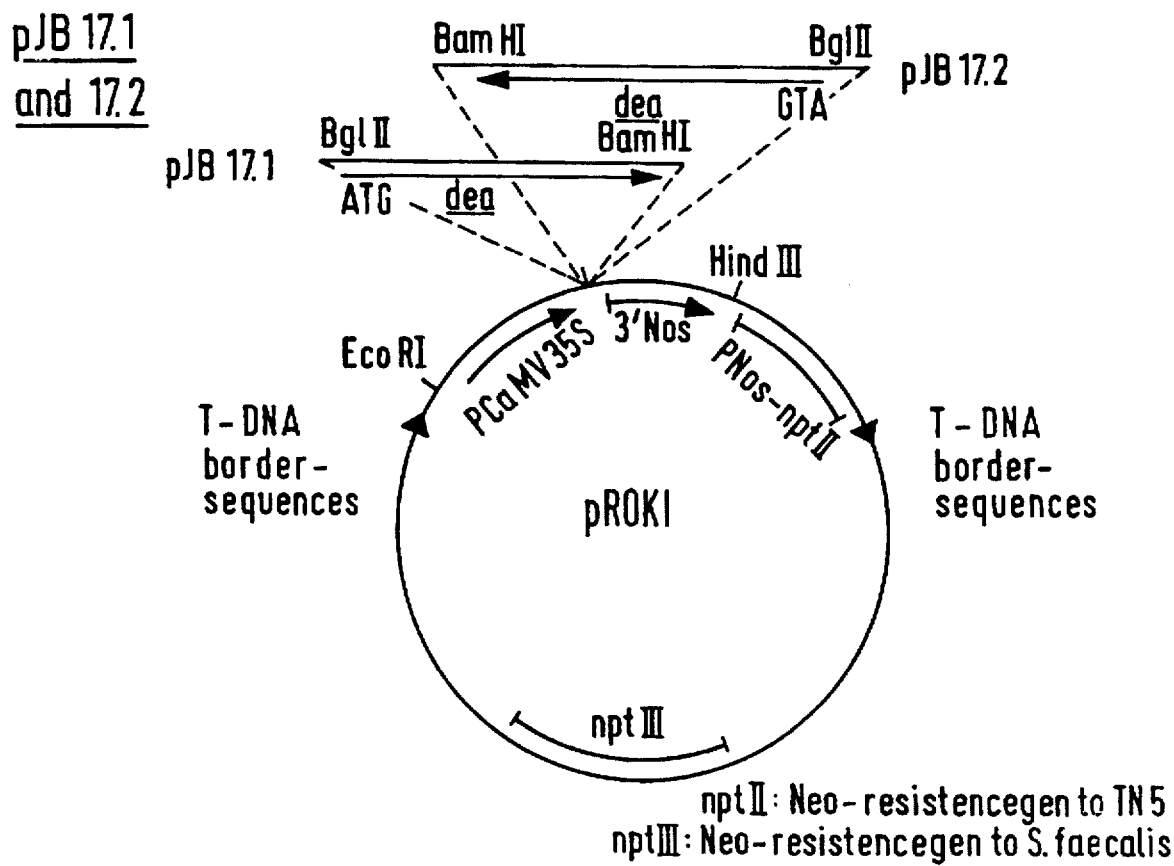
FIG. 2 shows restriction maps of vectors used in the invention and cleavage/ligation for preparing vectors of the invention.
Figure 2:
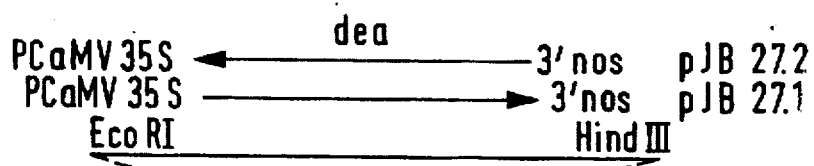
Figure 2:
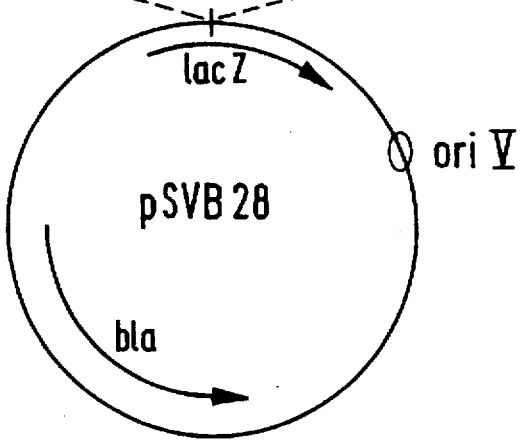

Example 1: Fusion of the deacetylase encoding region with eucaryotic transcription signals The plasmid pPRI (see EP-0.257.542) was isolated from an *E. coli* strain and cleaved with BamHI and BgIII. The digested DNA was separated on an agarose gel, and an 0.9 kb fragment was isolated from the gel. The vector pROKI (Baulcombe et al., Nature 321, 446–449, 1986) was also restricted with BamHI. The two batches were combined and ligated. The ligation mixture was transformed into *E. coli* S17.1 (Simon et al., Bio/Technology 1, 784–791, 1983). Colonies growing on kanamycin-containing media were transferred to nitrocellulose filters, incubated for 12 hours at 37° C. and then lysed. The DNA of the bacteria was fixed on the filter. The 0.9 kb fragment isolated from the agarose gel was made single-stranded by incubation at 100° C. The missing strand was then synthesized onto the existing strand using Klenow polymerase and digoxigenin-labeled nucleotides. The labeled strand was used as a sample for hybridizing with the bacterial DNA bound to the filter. Hybridizing clones could be detected with the aid of an antibody reaction. The DNA of the positive clones were isolated by means of Qiagen lysis and digested with BamHI/EcoRI as well as BamHI/HindIII. This restriction allows the orientation of the inserted 0.9 kb fragment to be determined. The plasmid in orientation I was designated pIB17.1, that of orientation II as pIB17.2 (see FIG. 2).

Example 2: Proof of the deacetylation of N-acetyl-PTC and N-acetyl-PTT by the deacetylase gene It was possible to demonstrate that the eucaryotic transcription signals cloned in vector pROKI also allow expression in *R. meliloti*, *A. tumefaciens* and *E. coli*.

The plasmids pIB17.1 and pIB17.2 were therefore transferred into *Rhizobium meliloti* strain 2011 by means of a 2-factorial cross. By incubation of *R. meliloti* wild type strains with radiolabeled N-acetyl-PTC, it was possible to demonstrate that this strain does not deacetylate N-acetyl-PTC. (After incubation of PIB17.1-carrying strains with N-acetyl-PTC and N-acetyl-PTT, deacetylation can be detected by thin-layer chromatography). It was also possible to demonstrate that *R. meliloti* reacts highly sensitively to PTC and PTT. Deacetylation can therefore also be detected via inhibition of the *R. meliloti* glutamine synthesase, by the PTC which is liberated.

Example 3: Transfer of the modified deacetylase gene into *Nicotiana tabacum*

The deacetylase gene modified as in Example 1 was transferred into *A. tumefaciens* LBA4404 by means of a 2-factorial cross. The resulting strains LBA4404/17.1 and LBA4404/17.2 were used for incubating leaf discs of *Nicotiana tabacum*, which were transferred after 3 days to a kanamycin-containing shoot induction medium. Regenerating kanamycin-resistant shoots can be tested for the presence of the deacetylase gene by Southern hybridization. After treatment with N-acetyl-PTC or N-acetyl-PTT, the plants are then destroyed by the PTC, or PTT, which is liberated.

Example 4: Construction of a vector for the transient expression of the modified deacetylase gene in *E. coli* and tobacco protoplasts The modified deacetylase gene from pIB17.1 and pIB17.2 was cut out of the plasmids by digestion with EcoRI/HindIII. The restricted DNA was separated in an agarose gel and an 0.9 kb fragment was isolated in each case. The vector pSVB28 (Arnold and Pühler, Gene 70, 171–179, 1988) was also digested with EcoRI/HindIII. The two batches were combined and ligated. After transformation into the β-galactosidase-negative *E. coli* strain JMB3, all clones which carried the vector turned blue, while clones which carried a vector into which the deacetylase gene had been inserted remained white. The DNA was isolated from the clones which had been identified in this way and digested with EcoRI/HindIII. The clones which contained the modified deacetylase gene could be recognized on the basis of the restriction pattern. The vectors which had been constructed are termed pIB27.1 and pIB27.2 (see FIG. 2). They exist in *E. coli* in a large number of copies.

Example 5: Transient expression of the modified deacetylase gene in tobacco protoplasts The plasmid DNA was isolated from the *E. coli* strains constructed in Example 4. Young tobacco leaves were incubated with digestion enzymes for 20 h. The protoplasts which get disengaged from the leaf skeleton were purified and incubated with polyethylene glycol (PEG) and the isolated DNA in a transfer buffer. The protoplasts were then washed and taken up in a culture liquid (K3 medium). After incubation for 3 days under weak illumination, the regenerating protoplasts were lysed and the crude extracts were incubated with radiolabeled N-acetyl-PTC and N-acetyl-PTT. The deacetylated PTC or PTT can be detected by thin-layer chromatography.

Example 6: Method for the production of male-sterile crop plants using the deacetylase gene from *S. viridochromogenes* under the control of a tapetum-specific promoter.

The deacetylase gene from *Streptomyces viridochromogenes* is fused with a tapetum-specific promoter from *Nicotiana tabacum* and introduced into tobacco cells by means of agrobacteria-mediated leaf disc transformation. The plants regenerating from these cells are sprayed with N-acetyl-PTC or N-acetyl-PTT at any desired point in time before anthesis. It can be shown that N-acetyl-PTC is stable in the plant cell and transported into all cells. None of the two substances has noticeable negative consequences for the wild type plant. As soon as the first tapetum cells are formed, they start to express the deacetylase gene. The N-acetyl-PTC or N-acetyl-PTT stored in the cell is deacetylated by the enzyme and so converted into its active form. It inhibits the glutamine synthetase of the cells and so results in rapid destruction. Mature pollen can no longer be formed. In addition, the formation of deacetylase is also interrupted. Cells in the vicinity should not be affected. If the plant is not treated with N-acetyl-PTC or N-acetyl-PTT, it is fully fertile. This makes compensation for the ms (male sterility) by a gene of the male crossing partner unnecessary. At the same time, there exists an accurately defined mutation which has no consequences on the vitality and usefulness of the plant.

Example 7: Identification of tissue-specific promoters in transgenic plants

Tissue-specific promoters can be identified directly in the plant with the aid of the deacetylase gene from *Streptomyces viridochromogenes*.

The deacetylase gene is cloned, without a promoter, to the right or left end of a disarmed T-DNA in such a way that a promoter which is located at the insertion site of the T-DNA in the plant genome can read into the gene and so bring about its expression. Transgenic plants are cloned via the propagation of cuttings. One clone is treated with N-acetyl-PTC or N- acetyl-PTT and examined for tissue which may be in the process of dying. Using reverse PCR, the gene which has been affected can be multiplied from a clone which has not been treated with N-acetyl-PTC or N-acetyl-PTT and isolated (Kahl and Weising, Gentransfer bei Pflanzen [Gene Transfer in Plants], Biologie in unserer Zeit, No. 6, p. 181, 1988).

Example 8: Detection of N-acetyl-phosphinothricin (PPT)-deacetylase activity in soil samples Soil samples of 500 mg each (sandy loam, Schwanheimer Düune) were adjusted to 40% of their maximum water capacity and treated with 5 µl of a 15 mM stock solution of $^{14}$[C]-L-N-acetyl-PPT. The test samples were incubated at 28° C. for various periods of time (0 hours, 4, 7, 11 and 14 days) and subsequently worked up by extraction with 1×500 µl and 1×250 µl of water. 14 µl aliquots from the combined aqueous supernatants were applied to thin-layer chromatography plates (HPTLC cellulose, Merck) and developed 2×in n-propanol: 25% ammonia=3:2 as the mobile phase. The assays were evaluated by autoradiography. It was possible to identify N-acetyl-PPT and PPT by comparing the $R_f$ values of the radioactive spots with the corresponding reference substances. It emerged that N-acetyl-PPT in the soil is metabolized within 14 days almost completely to give PPT. In contrast, in a control assay with sterile soil samples (soil 4 hours at 200° C.), the substance proved to be completely stable.

Example 9: Isolation and identification of soil microorganisms having an N-acetyl-PPT-specific deacetylase activity 1 g samples of soil were extracted for 1 hour at room temperature using 10 ml 10 mM NaCl, 10 mM sodium phosphate buffer, pH=7.0. To select various groups of microorganisms, the soil supernatants were plated onto the following agar media and used for inoculating enrichment cultures in Erlenmeyer flasks with the corresponding liquid media:

(1) MS1 medium (for eubacteria):
5 mM glucose
5 mM succinate
10 mM glycerol
1 g/l NH$_4$Cl
50 ml/l solution A
25 ml/l solution B
Solution A:
  50 g/l K$_2$HPO$_4$
Solution B:
  2.5 g/l MgSO$_4$
  0.5 g/l NaCl
  25 ml/l trace elements (2) Chitin medium (for actinomycetes and streptomycetes as well as chitinovorous bacteria):
10 g/l crab chitin
1 g/l (NH$_4$)$_2$SO$_4$
0.5 g/l MgSO$_4$
50 ml/l solution A
1 ml/l trace elements (3) Antibiotics medium (for higher fungi):
20 g/l malt extract
10 g/l glucose
2 g/l yeast extract
0.5 g/l (NH$_4$)$_2$SO$_4$
50 #g/ml tetracyclin All media contained 5 mM N-acetyl-PPT. The agar plates and the liquid cultures were incubated for 3–5 days at 28° C.

20 individual colonies were isolated from each of the selective agar plates and transferred into 5 ml liquid cultures with the corresponding medium. The cells were allowed to grow for 3–5 days and then centrifuged at 10,000 rpm, and the supernatants were examined in the aminoacid analyzer (Biotronic LC 5001) for the formation of PPT. In this manner, a PPT-positive culture (CB 10) was isolated from a selection with chitin medium.

The deacetylase activity of the cells of this culture were subsequently additionally tested by biotransformation with $^{14}$[C]-L-N-acetyl-PPT as the substrate. To do this, 1.5 ml of the culture were centrifuged as above, the cell pellet was washed 1×in 10 mM NaCl, 10 mM sodium phosphate buffer, pH=7.0, and resuspended in 100 µl of the same buffer. 10 µl of the suspension were treated with 10 µl of an 0.25 mM solution of $^{14}$[C]-L-N-acetyl-PT and the mixture was incubated for 15 hours at 28° C. The bacteria were then centrifuged off, and 7 µl of the supernatant were analyzed by thin-layer chromatography and autoradiography as described in Example 1. A virtually quantitative reaction of N-acetyl-PPT into PPT could be observed. In addition, the assay showed that the deacetylase found accepts the L enantiomer of the acetylated PPT as substrate.

To further purify the strain with the desired deacetylase activity, the culture CB 10 was plated onto LB agar (10 g/l tryptone, 5 g/l yeast extract, 10 g/l NaCl, 15 g/l agar) and incubated for 2 days at 28° C. 10 individual colonies were isolated from the plate, transferred to chitin liquid medium, and the cultures were tested for N-acetyl-PPT deacetylase activity as described above. The deacetylase-positive isolates were replated to check for uniformity of the culture. The strain with the highest deacetylase activity was identified as *Xanthomonas maltophilia* (DSM deposit No. DSM 7192).

The enrichment cultures in the soil samples in the various liquid media were tested for deacetylation of N-acetyl-PPT as described above. Only the chitin medium cultures proved to be deacetylase-positive. After these cultures were plated onto chitin agar, a total of 40 individual colonies was isolated, grown in chitin liquid medium and subsequently tested for deacetylase activity. Six positive isolates were found (BoK1, BoK5, BoK9, BCÜ1, BCÜ2, BCÜ3), from which the active pure cultures were obtained by replating onto agar plates and culturing further on individual colonies (see above). The strain with the highest deacetylase activity was identified as *Microbacterium imperiale* (DSM deposit No. 7191)

Example 10: N-Acetyl-PPT deacetylase enzyme assays with the isolated microorganisms 5 ml precultures of strains BoK1 and BoK5 were grown in LB medium overnight at 28° C., and 0.5 ml aliquots were transferred to 20 ml of LB medium or 20 ml of chitin medium containing 1 mM N-acetyl-PPT. The LB cultures were incubated for 15 hours and the chitin cultures for 4 days in 100 ml Erlenmeyer flasks at 28° C. and 150 rpm. The cells were subsequently harvested by centrifugation for 10 minutes at 10,000 rpm, the cell pellets were washed 1×in 10 ml mM NaCl, 10 mM sodium phosphate buffer, pH=7.0, weighed and resuspended in 100 mM tris/HCl, pH=8.0 at c=100 mg/ml. The suspensions were mixed with 1 volume of 100 mM N-acetyl-PPT and incubated in 50 ml Erlenmeyer flasks for 24 hours at 28° C. and 220 rpm. The cells were separated by centrifugation for 10 minutes at 5000 rpm, and the PPT content in the supernatants was then determined in the aminoacid analyzer (see Example 9). The results are compiled in Table 2.

TABLE 2

N-Acetyl-PPT deacetylase assays with soil microorganisms

| Strain: | Medium: | Concentration of PPT in the supernatant | |
|---|---|---|---|
| | | [mM]: | [%]*: |
| BoK1 | LB | 0.7 | 2.7 |
| BoK1 | Chitin | 13.9 | 55.5 |
| BoK5 | LB | 6.0 | 23.9 |
| BoK5 | Chitin | 14.3 | 57.2 |

*: based on the L-enantiomer in the N-acetyl-PPT racemate.

Example 11: N-Acetyl-PPT deacetylase enzyme assays with actinomycetes

N-Acetyl-PPT-specific deacetylase activities were also found during fermentation tests with the two actinomycetes strains *Actinoplanes liguriae* (IFO No. 13997) and *Actinoplanes sp.* (Strain Collection Zentralforschung No. A 1015) in the presence of N-acetyl-PPT and by biotransformation with $^{14}$[C]-L-N-acetyl-PPT as the substrate.

To determine the conversion rates, biotransformations were carried out on the two strains as described in Example 3. The following media were used:

Medium A:
0.2% yeast extract
0.2% meat extract
0.4% polypeptone (from soya meal)
1% glucose
Medium B:
20 g/l oat flakes
1 ml/l trace elements
The results are compiled in Table 3.

TABLE 3

N-Acetyl-PPT deacetylase assays with actinomycetes

| Strain: | Medium: | Concentration of PPT in the supernatant | |
|---|---|---|---|
| | | [mM]: | [%]*: |
| *Actinoplanes liguriae* (IFO No. 13997) | A | 3.3 | 13.2 |
| *Actinoplanes liguriae* (IFO No. 13997) | B | 7.6 | 30.4 |
| *Actinoplanes sp.* (No. A 1015) | A | 11.0 | 44.0 |
| *Actinoplanes sp.* (No. A 1015) | B | 2.7 | 10.8 |

*: based on the L enantiomer in the N-acetyl-PPT racemate

Further isolates from soil with n-Acetyl-PPT-specific deacetylase activity
from culture CB 10:
*Clavibacter michiganense insidiosum*
*Agrobacterium tumefaciens*
*Agrobacterium oxydans*
*Bacillus amyloliquefaciens*
*Bacillus macerans*
from culture BoK1:
*Alcaligenes faecalis*
*Escherichia coli*
from culture BoK5:
*Staphylococcus hominis*
from culture BCÜ1:
*Micrococcus luteus A*
*Acinetobacter johnsonii*
*Microbacterium laeraniformans*
from culture BCÜ2:
*Acinetobacter calcoaceticus*

We claim:

1. A process for the production of a transgenic plant with selectively destroyable tissue, which comprises the following steps:
   a) transforming a plant cell so as to obtain a plant cell comprising a tissue-specific promoter and a deacetylase coding region wherein the tissue specific promoter is 5' of and operably linked to the deacetylase coding region wherein the deacetylase is capable of deacetylating N-acetyl-PTC or N-acetyl-PTT,
   b) regenerating from the cell a plant having tissue portions in which the deacetylase coding region is expressed as a deacetylase, and
   c) treating the plant with N-acetyl-PTC or N-acetyl PTT, wherein the expressed deacetylase converts N-acetyl-PTC or N-acetyl-PTT into PTC or PTT in the tissue portions, causing death of the tissue portions.

2. A process for expressing a deactylase gene in a tissue-specific manner, which comprises the following steps:
   a) transforming a plant cell so as to obtain a plant call comprising a tissue-specific promoter and a deacetylase coding region wherein the tissue-specific promoter is 5' of and operably linked to the deacetylase coding region wherein the deacetylase is capable of deacetylating N-acetyl-PTC or N-acetyl-PTT,
   b) regenerating from the cell a plant having tissue portions in which the deacetylase coding region is expressed as a deacetylase, and
   c) treating the plant with N-acetyl-PTC or N-acetyl PTT, wherein the expressed deacetylase converts N-acetyl-PTC or N-acetyl-PTT into PTC or PTT in the tissue portions, preventing functioning of the tissue portions.

3. A process for the production of a transgenic plant with selectively destroyable tissue, wherein the plant has phosphinothricin resistance, comprising:
   a) transforming a plant cell so as to obtain a plant cell comprising a tissue-specific promoter and a deacetylase coding region wherein the tissue-specific promoter is 5' of and operably linked to the deacetylase coding region wherein the deacetylase is capable of deacetylating N-acetyl-PTC or N-acetyl-PTT.
   b) regenerating from the cell a plant having tissue portions in which the deacetylase coding region is expressed as a deacetylase, and
   c) treating the plant with N-acetyl-PTC or N-acetyl-PTT wherein the expressed deacetylase converts N-acetyl-PTC or N-acetyl-PTT into PTC or PTT in the tissue portions, or treating the plant with PTC or PTT, causing death of the tissue portions.

4. The process as claimed in claim 2, wherein the deacetylase gene originates from *E. coli* and the plant is treated with N-acetyl-PTC or with PTC.

5. The process as claimed in claim 2, wherein the deacetylase gene originates from *Arthrobacter* and the plant is treated with N-acetyl-PTC or with PTC.

6. The process as claimed in claim 1, wherein the deacatylase gene originates from *E. coli* and the plant is treated with N-acetyl-PTC or with PTC.

7. The process as claimed in claim 1, wherein the deacetylase gene originates from *Arthrobacter* and the plant is treated with N-acetyl-PTC or with PTC.

8. The process as claimed in claim 1, wherein the deacetylase gene originates from *Streptomyces* viridochromogenes and the plant is treated with N-acetyl-PTT or with PTT.

9. The process as claimed in claim 2, wherein male-sterile plants are produced.

10. The process as claimed in claim 9, wherein the deacetylase gene is under the control of a tapetum promoter.

11. A process for preventing the development of targeted parts of plants which comprises:

producing a tranagenic plant which contains a deacetylase gene under the control of a tissue-specific promoter; and applying N-acetyl-PTC or N-acetyl PTT to the plant to produce targeted inhibition of glutamine synthetase in the plant, which prevents the development of targeted parts of the plant.

12. A transgenic plant comprising exogenous DNA encoding a deacetylase capable of deacetylating N-acetyl-PTC or N-acetyl-PTT, wherein the plant expresses the DNA.

13. The plant of claim 12 wherein a tissue specific promoter is located 5' of and operably linked to the exogenous DNA.

14. A transgenic plant cell comprising exogenous DNA encoding a deacetylase capable of deacetylating N-acetyl-PTC or N-acetyl-PTT, wherein the plant cell expresses the DNA.

15. The plant cell of claim 14 wherein a tissue specific promoter is located 5' of and operably linked to the exogenous DNA.

16. A plant comprising a plant cell of claim 14 or 15 which expresses the DNA.

17. A plant obtainable from the process of claim 1.

18. A plant obtainable from the process of claim 3.

19. A vector comprising an isolated DNA molecule encoding a deacetylase capable of deacetylating N-acetyl-PTC or N-acetyl-PTT.

20. The vector of claim 19 wherein a tissue specific promoter is located 5' of and operably linked to the isolated DNA molecule.

21. A plant cell comprising a vector of claim 19 or 20 which expresses the isolated DNA molecule.

22. A plant comprising the plant cell of claim 21 which expresses the isolated DNA molecule.

23. A plant comprising a vector of claim 19 or 20 which expresses the DNA.

24. A positive selection system for detecting clone insertion events or transpositions wherein the deacetylase gene is inactivated, which comprises:

transforming plant cells so as to obtain transformed plant cells comprising a deacetylase coding region;

regenerating plants from the transformed plant cells;

treating the regenerated plants with N-acetyl PTC or PTC or N-acetyl PTT or PTT;

selecting those plants in which the deacetylase coding region is inactivated, and there is no death of tissue portions of the plants from the treatment.

25. A positive selection system for detecting clone insertion events or transpositions wherein the deacetylase gene is inactivated, which comprises:

transforming plant cells so as to obtain transformed plant cells comprising a deacetylase coding region;

treating the transformed plant cells with N-acetyl PTC or PTC or N-acetyl PTT or PTT;

selecting those cells in which the deacetylase coding region is inactivated, and there is no death of the cells from the treatment.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 932 base pairs
( B ) TYPE: nucleic acid
( C ) STRANDEDNESS: single (D) TOPOLOGY: linear (x i) SEQUENCE DESCRIPTION: SEQ ID NO:1:

```
AGATCTGAGC GGAGAGCGCA TGGCATCGTC GGAGTTGGAG CTCGTGCGGG AACTGATCGG    60
GCTCAACTGG CACACCCGCA ACGGCGATGT GGAGCCACGC CGGGTGGCCT ACGACCGAGC   120
CCAGGAGGCC TTCGGCACC  TGGGCCTGCC CCCCGGCGAG ACCGTCGTGA TCGGCGACTG   180
CTCGGCGGAG TGGGTACGGC CCGCCCAGGA GGACGGCAGG ACCCTGCTGT ACCTGCACGG   240
CGGTTCGTAC GCCCTCGGAT CGCCGCAGTC GCACCGCCAT CTGTCCAGCG CGCTGGGCGC   300
GGCGGCCGGG GCGGCGGTGC TCGCCCTGCA CTACCGCAGG CCGCCCGAGT CTCCCTTCCC   360
GGCGGCGGTG GAGGACGCCG TGGCGGCCTA CCGGATGCTG CGGGAGCGGG GCCTGCCGCC   420
GGGGCGGATC ACCTTCGCCG GTGACTCGGC CGGCGCGGGC CTCGCCGTCG CCGCCCTCCA   480
GGTGCTGCGC GACGCCGGGG ACCCGCTGCC GGCCGCCGCG GTGTGCATCT CGCCCTGGGC   540
CGACCTGGCC TGCGAGGGCG CCTCGCACGT CACCCGCAAG GAGCGCGAGA TCCTCCTGGA   600
CACCGAGGAC CTGCTCCGCA TGGCGGGGCG CTACCTGGCC GGCACCGATC CCAGGAACCC   660
CCTGGCCTCG CCCGCCCACG GCGATCTGAC CGGTCTGCCC CCCCTGCTCA TCCAGGTCGG   720
TTCCGAGGAA GTCCTGTACG ACGACCCCCG GGCGCTGGAA CAGGCGGCGC TCAAGGCGGG   780
CGTACCGGTC ACCTTCGACG AGTGGCCGGA GATGTTCCAC GTCTGGCACT GGTACCACCC   840
GGTGCTCCCC GAGGGGCGTG CCGCCGTCGA GACGGCGGGC GTGTTCCTGC GCCGCGCCAC   900
CGAGGAGGGC GAGCGGTGAC CGACTGGATC CT                                 932
```